(12) United States Patent
Martins et al.

(10) Patent No.: US 9,328,036 B2
(45) Date of Patent: May 3, 2016

(54) HYDROCARBON CONVERSION PROCESS INCLUDING CATALYST REGENERATION

(71) Applicant: UOP LLC, Des Plaines, IL (US)

(72) Inventors: Susie C. Martins, Carol Stream, IL (US); Erin M. Broderick, Arlington Heights, IL (US); Douglas A. Nafis, Mt. Prospect, IL (US); Kaitlin M. DeSalvo, Chicago, IL (US); Stuart Smith, Lake Zurich, IL (US); Alakananda Bhattacharyya, Glen Ellyn, IL (US)

(73) Assignee: UOP LLC, Des Plaines, IL (US)

( * ) Notice: Subject to any disclaimer, the term of this patent is extended or adjusted under 35 U.S.C. 154(b) by 240 days.

(21) Appl. No.: 14/270,057

(22) Filed: May 5, 2014

(65) Prior Publication Data

US 2015/0315095 A1    Nov. 5, 2015

(51) Int. Cl.
| | |
|---|---|
| *C07C 2/60* | (2006.01) |
| *C07C 2/62* | (2006.01) |
| *C07C 2/68* | (2006.01) |
| *C07C 2/70* | (2006.01) |

(52) U.S. Cl.
CPC ............... *C07C 2/62* (2013.01); *C07C 2531/22* (2013.01)

(58) Field of Classification Search
CPC .............. C07C 2/60; C07C 2/62; C07C 2/68; C07C 2/70
USPC ......... 585/456, 457, 458, 459, 460, 462, 464, 585/465, 466, 723, 726, 730, 731
See application file for complete search history.

(56) References Cited

U.S. PATENT DOCUMENTS

| | | |
|---|---|---|
| 2,887,500 A | 5/1959 | McEntee |
| 4,547,595 A | 10/1985 | Chang |
| 4,824,657 A | 4/1989 | Jadhav |
| 7,651,970 B2 | 1/2010 | Elomari et al. |
| 7,674,739 B2 | 3/2010 | Elomari et al. |
| 7,674,740 B2 | 3/2010 | Harris et al. |
| 7,678,727 B2 | 3/2010 | Harris et al. |

(Continued)

FOREIGN PATENT DOCUMENTS

| | | |
|---|---|---|
| CN | 102666444 A | 9/2012 |
| JP | 55001870 | 1/1980 |

OTHER PUBLICATIONS

Schmidt et al., "Disproportionation of Light Paraffins," Energy & Fuels (2008), vol. 22, 1812-1823.

(Continued)

*Primary Examiner* — Thuan D Dang

(57) ABSTRACT

A hydrocarbon conversion process is described. The process includes contacting a hydrocarbon feed with an acidic catalyst under hydrocarbon conversion conditions in a hydrocarbon conversion zone. The hydrocarbon feed reacts to form a mixture comprising reaction products, the acidic catalyst, and deactivated acidic catalyst containing conjunct polymer. The mixture is separated into at least two streams, a first stream comprising the reaction products and a second stream comprising the deactivated acidic catalyst. The reaction products are recovered. The deactivated acidic catalyst is contacted with at least one silane or borane compound in a regeneration zone under regeneration conditions, the conjunct polymer reacting with the at least one silane or borane compound resulting in a catalyst phase and an organic phase containing the conjunct polymer and at least one silyl or boryl compound.

19 Claims, 1 Drawing Sheet

(56) References Cited

U.S. PATENT DOCUMENTS

| | | |
|---|---|---|
| 7,691,771 B2 | 4/2010 | Harris et al. |
| 7,727,925 B2 | 6/2010 | Elomari et al. |
| 7,732,363 B2 | 6/2010 | Elomari et al. |
| 7,732,364 B2 | 6/2010 | Chang et al. |
| 7,737,067 B2 | 6/2010 | Elomari et al. |
| 7,737,363 B2 | 6/2010 | Kambe |
| 7,754,636 B2 | 7/2010 | Elomari et al. |
| 7,825,055 B2 | 11/2010 | Elomari et al. |
| 7,884,045 B2 | 2/2011 | Harris et al. |
| 7,956,002 B2 | 6/2011 | Elomari et al. |
| 7,995,495 B2 | 8/2011 | Lin |
| 8,507,396 B2 | 8/2013 | Elomari et al. |
| 8,524,623 B2 | 9/2013 | Timken et al. |
| 2007/0142211 A1 | 6/2007 | Elomari et al. |
| 2007/0142213 A1 | 6/2007 | Elomari et al. |
| 2007/0142215 A1 | 6/2007 | Harris et al. |
| 2007/0142216 A1 | 6/2007 | Harris et al. |
| 2007/0142217 A1 | 6/2007 | Elomari et al. |
| 2007/0142218 A1 | 6/2007 | Harris et al. |
| 2007/0249485 A1 | 10/2007 | Elomari et al. |
| 2007/0249486 A1 | 10/2007 | Elomari et al. |
| 2010/0130804 A1 | 5/2010 | Timken et al. |
| 2010/0147740 A1 | 6/2010 | Elomari et al. |
| 2012/0283500 A1 | 11/2012 | Liu et al. |

OTHER PUBLICATIONS

Iranpoor et al. "Diphenylphosphinite ionic liquid (IL-OPPh2): A solvent and ligand for palladium . . . " Journal of Organometallic Chemistry(2010), 695(6), 887-890.

Gevorgyan et al. "Reduction of Alkoxysilanes, Halo-silanes and -Germanes with Lithium . . . " Journal of Organometallic Chemistry (1985), vol. 284, C31-C32.

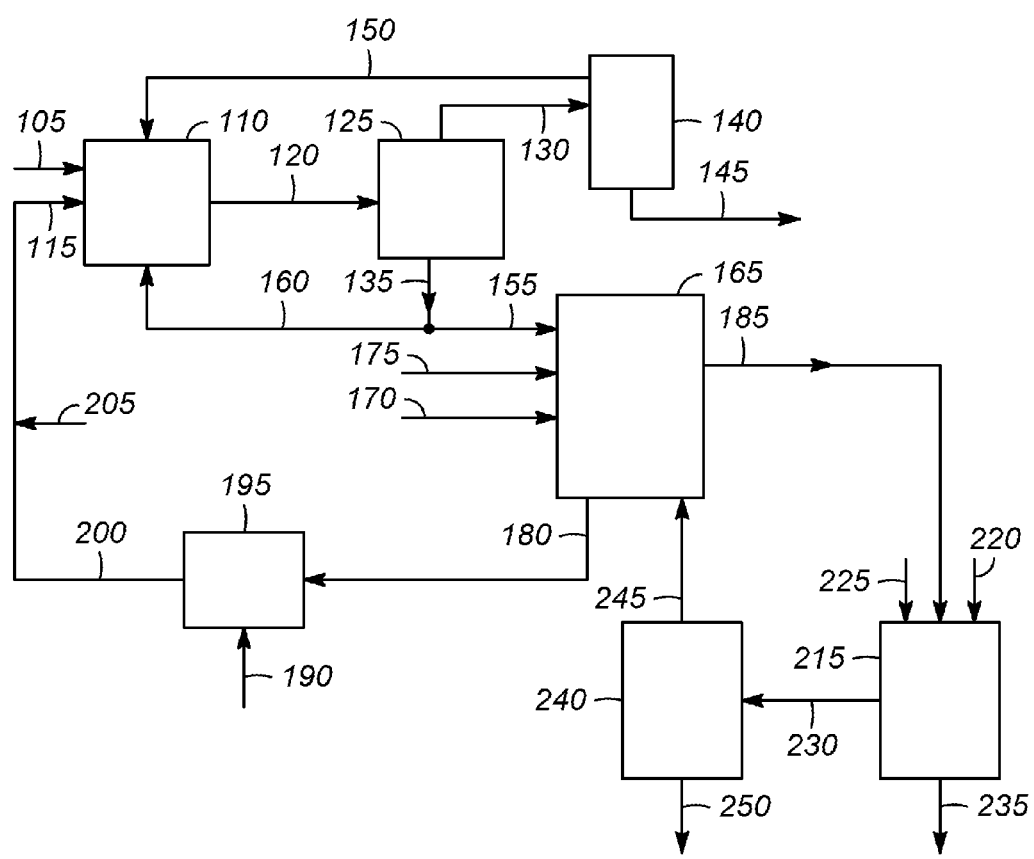

HYDROCARBON CONVERSION PROCESS INCLUDING CATALYST REGENERATION

BACKGROUND OF THE INVENTION

Hydrocarbon conversion processes are often catalyzed using acidic catalysts. For example, commercially, the alkylation of isoparaffins is catalyzed by acids such as sulfuric acid and hydrofluoric acid. Conjunct polymer (acid soluble oils, (ASO) also known as red oil) forms as a byproduct of the alkylation reaction, as well as other hydrocarbon reactions. When too much conjunct polymer is present, the acid catalyst loses its effectiveness. The acid must be replaced with stronger acid, or the conjunct polymer must be removed in order to reactivate the catalyst. With sulfuric acid as the catalyst, the ASO is burned, and with hydrofluoric acid, the hydrofluoric acid is distilled away from the ASO. Sulfuric acid and hydrofluoric acid are hazardous and corrosive, and their use in industrial processes requires a variety of environmental controls.

There has been a move to replace the use of sulfuric acid and hydrofluoric acid with more environmentally friendly materials.

One such process utilizes acidic ionic liquids as catalysts in hydrocarbon conversion processes, such as alkylation, isomerization, disproportionation, and oligomerization. Conjunct polymers are byproducts of the hydrocarbon reaction using ionic liquids, and they form a complex with the ionic liquid catalyst. The ionic liquid catalyst loses its effectiveness over time as the amount of conjunct polymer increases. It must then either be replaced or regenerated. Because ionic liquids are typically fairly expensive, processes for regenerating the ionic liquid catalysts are needed.

A variety of methods for regenerating ionic liquids have been developed. The ionic liquid containing the conjunct polymer could be contacted with a reducing metal (e.g., Al), an inert hydrocarbon (e.g., hexane), and hydrogen and heated to about 100° C. The conjunct polymer will be transferred to the hydrocarbon phase, allowing for the conjunct polymer to be removed from the ionic liquid phase. See e.g., U.S. Pat. No. 7,651,970; U.S. Pat. No. 7,825,055; U.S. Pat. No. 7,956,002; and U.S. Pat. No. 7,732,363.

Another method involves contacting the ionic liquid containing the conjunct polymer with a reducing metal (e.g., Al) in the presence of an inert hydrocarbon (e.g. hexane), but in the absence of added hydrogen, and heating to about 100° C. The conjunct polymer will be transferred to the hydrocarbon phase, allowing for the conjunct polymer to be removed from the ionic liquid phase. See e.g., U.S. Pat. No. 7,674,739.

Still another method of regenerating the ionic liquid involves contacting the ionic liquid containing the conjunct polymer with a reducing metal (e.g., Al), HCl, and an inert hydrocarbon (e.g. hexane), and heating to about 100° C. The conjunct polymer will be transferred to the hydrocarbon phase, allowing for the CP to be removed from the IL phase. See e.g., U.S. Pat. No. 7,727,925.

The ionic liquid can be regenerated by adding a homogeneous metal hydrogenation catalyst (e.g., $(PPh_3)_3RhCl$) to the ionic liquid containing the conjunct polymer and an inert hydrocarbon (e.g. hexane). Hydrogen would be introduced, and the conjunct polymer would be reduced and transferred to the hydrocarbon layer. See e.g., U.S. Pat. No. 7,678,727.

Another method for regenerating the ionic liquid involves adding HCl, isobutane, and an inert hydrocarbon to the ionic liquid containing the conjunct polymer and heating to about 100° C. The conjunct polymer would react to form an uncharged complex, which would transfer to the hydrocarbon phase. See e.g., U.S. Pat. No. 7,674,740.

The ionic liquid could also be regenerated by adding a supported metal hydrogenation catalyst (e.g. Pd/C) to the ionic liquid containing the conjunct polymer and an inert hydrocarbon (e.g. hexane). Hydrogen would be introduced and the conjunct polymer would be reduced and transferred to the hydrocarbon layer. See e.g., U.S. Pat. No. 7,691,771.

Still another method involves adding a basic reagent that displaces the conjunct polymer and is a part of the regeneration of the catalyst. The basic reagents are described as nitrogen-containing compounds such as amines, pyridinium compounds, or pyrrolidinium compounds. For example, a suitable substrate (e.g. pyridine) is added to the ionic liquid containing the conjunct polymer. After a period of time, an inert hydrocarbon would be added to wash away the liberated conjunct polymer. The ionic liquid precursor [butylpyridinium][Cl] would be added to the ionic liquid (e.g. [butylpyridinium] [$Al_2Cl_7$]) containing the conjunct polymer followed by an inert hydrocarbon. After a given time of mixing, the hydrocarbon layer would be separated, resulting in a regenerated ionic liquid. The solid residue would be converted to catalytically active ionic liquid by adding $AlCl_3$. See e.g., U.S. Pat. No. 7,737,363 and U.S. Pat. No. 7,737,067.

Another method involves adding the ionic liquid containing the conjunct polymer to a suitable substrate (e.g. pyridine) and an electrochemical cell containing two aluminum electrodes and an inert hydrocarbon. A voltage would be applied and the current measured to determine the extent of reduction. After a given time, the inert hydrocarbon would be separated, resulting in a regenerated ionic liquid. See, e.g., U.S. Pat. No. 8,524,623.

All of these regeneration approaches have drawbacks. Many of them cannot achieve above 90% conversion of the conjunct polymer, which then builds up in the process. Of those that can provide high levels of conversion, hydrogenation of the spent ionic liquid with supported (e.g., U.S. Pat. No. 7,691,771) and unsupported (e.g., U.S. Pat. No. 7,678,727) hydroprocessing catalysts may result in the active catalytic metals being extracted into the ionic liquid phase. Many catalyst supports also react irreversibly with the chloroaluminate anion of the ionic liquid. Although the use of metallic aluminum for regeneration (e.g., U.S. Pat. No. 7,995,495) is effective, it introduces undesirable solids handling issues into the refinery. Finely divided aluminum is pyrophoric and presents safety issues in a refining environment. This approach also results in the creation of additional $AlCl_3$, which has to be removed from the ionic liquid phase (e.g., U.S. Pat. No. 7,754,636) to avoid building up to a molar ratio relative to the ionic liquid cation at which solids will start precipitating out of solution and cause plugging issues. Electrochemical approaches (e.g., U.S. Pat. No. 8,524,623) are not economically viable at commercial scales.

Therefore, there remains a need for additional methods of regenerating ionic liquids used as catalysts in reactions.

SUMMARY OF THE INVENTION

One aspect of the present invention is a hydrocarbon conversion process. In one embodiment, the process includes contacting a hydrocarbon feed with an acidic catalyst under hydrocarbon conversion conditions in a hydrocarbon conversion zone. The acidic catalyst is selected from the group consisting of sulfuric acid, hydrofluoric acid, trifluoromethanesulfonic acid, phosphoric acid, boron trifluoride, and acidic ionic liquids. The hydrocarbon feed reacts to form a mixture comprising reaction products, the acidic catalyst, and deactivated acidic catalyst containing conjunct polymer. The mixture is separated into at least two streams, a first stream comprising the reaction products and a second stream comprising the deactivated acidic catalyst containing conjunct polymer. The reaction products are recovered. The deactivated acidic catalyst containing the conjunct polymer is contacted with at least one silane or borane compound in a regeneration zone under regeneration conditions, the conjunct polymer reacting with the at least one silane or borane compound resulting in a catalyst phase and an organic phase containing the conjunct polymer and at least one silyl or boryl compound.

BRIEF DESCRIPTION OF THE DRAWING

The FIGURE illustrates one embodiment of a hydrocarbon conversion process according to the present invention.

DETAILED DESCRIPTION OF THE INVENTION

Hydrocarbon conversion processes utilizing acidic catalysts frequently generate conjunct polymer which deactivates the acidic catalyst over time. The conjunct polymer must be removed in order to maintain the activity of the catalyst. Examples of hydrocarbon conversion processes in which this occurs include, but are not limited to, alkylation, oligomerization, isomerization, disproportionation, and reverse disproportionation.

It has been discovered that deactivated acidic catalysts containing conjunct polymer can be regenerated using a reagent that contains no metals and that reacts at mild conditions. In some embodiments, the reagent can be easily separated by gravity from the ionic liquid. When a liquid reagent is used, the process does not produce any net solids that have to be handled or treated. When solvents are used with liquid reagent, the liquid reagent can be easily separated from the solvent. In addition, the mild conditions under which the process can be performed may result in lower operating costs than processes requiring harsher conditions. The mild operating conditions may also result in lower capital costs due to the ability to use less expensive materials of construction.

By deactivated acidic catalysts containing conjunct polymer, we mean acidic catalysts that have been used in hydrocarbon conversion processes, and in which conjunct polymers have formed. Acidic catalysts which form conjunct polymers in hydrocarbon conversion processes include sulfuric acid, hydrofluoric acid, trifluoromethanesulfonic acid (triflic acid), phosphoric acid, boron trifluoride, and acidic ionic liquids. By conjunct polymer, we mean the olefinic, conjugated cyclic hydrocarbons that form as a byproduct of various hydrocarbon conversion processes, including but not limited to alkylation, oligomerization, isomerization, disproportionation, and reverse disproportionation.

By acidic ionic liquid, we mean an ionic liquid capable of catalyzing reactions typically carried out with an acid. As known in the art, acids such as sulfuric acid and hydrofluoric acid are often used to catalyze these reactions. These reactions include, e.g. alkylation, oligomerization, isomerization, disproportionation, and reverse disproportionation. Oftentimes the acids employed in these reactions have Hammett acidity functions ($H_o$) less than 7, or less than 5, or less than 3, or less than 0, or less than −3, or less than −5, or less than −7, or less than −9. If the ionic liquid does not possess an acidic proton in its structure (e.g. 1-butyl-3-methylimidazolium heptachloroaluminate), addition of an exogenous acid is acceptable, provided the Hammett acidity function ($H_o$) of the added acid is less than 7 within the ionic liquid, or less than 5, or less than 3, or less than 0, or less than −3, or less than −5, or less than −7, or less than −9. Acidic chloroaluminate-containing ionic liquids have a molar ratio of Al to cation greater than 1.

By the term about, we mean within 10% of the specified value, or within 5%, or within 1%.

The hydrocarbon conversion process involves contacting a hydrocarbon feed with the acidic catalyst. The feed reacts in the presence of the acidic catalyst, and this results in a mixture containing the reaction products, the acidic catalyst, and deactivated catalyst containing conjunct polymer.

The temperature is generally in the range of about −20° C. to about 250° C., and the pressure is generally in the range of about 0 MPa to about 13.8 MPa. The reaction time is typically in the range of a few seconds to hours. When the catalyst is an ionic liquid, the reaction time is a function of the degree of mixing, the reaction temperature, and the mass/volume ratio of liquid catalyst to hydrocarbon being reacted. Generally, increasing any of these conditions will increase the reaction rate. The reaction conditions and typical feeds for various hydrocarbon conversion processes are described in more detail below.

The hydrocarbon conversion reaction will proceed simply by contacting the hydrocarbon feed with the liquid acidic catalyst. When a liquid catalyst is used, the reaction rate without mixing is generally too slow under static conditions to be commercially viable. When mass transfer rate is controlling, the reaction rate can be substantially increased by increasing the mixing intensity of hydrocarbon feed and liquid catalyst. After a certain point, increasing the mixing intensity will not provide any additional benefit. Mixing intensity can be controlled using pumps, nozzles, impellers, flow configurations, and baffles. Baffles help to prevent a vortex from forming in the reactor, which would reduce the amount of mixing.

The contacting step may be practiced in laboratory scale experiments through full scale commercial operations. The process may be operated in batch, continuous, or semi-continuous mode. The contacting step can take place in various ways, with both countercurrent and co-current flow processes being suitable. For example, the reactants can be added individually, or some reactants may be combined or mixed before being combined or mixed with other reactants.

The mixture of the reaction products, the acidic catalyst, and deactivated catalyst containing conjunct polymer is then separated into at least two streams: a first stream containing the reaction products and a second stream containing the acidic catalyst and the deactivated acidic catalyst containing conjunct polymer.

The first stream containing the reaction products is recovered.

The second stream containing acidic catalyst and the deactivated acidic catalyst containing conjunct polymer is contacted with at least one silane or borane compound. The conjunct polymer reacts with the silane or borane compound, resulting in a catalyst phase and an organic phase containing the conjunct polymer and a silyl or boryl compound. The organic phase will typically also contain the solvent if present.

The contact of a silane or borane compound with an acidic catalyst that contains conjunct polymer releases the conjunct polymer from the acidic catalyst. When the acidic catalyst is an ionic liquid, the ionic liquid can then be reactivated with acid. Other acidic catalysts may also require reactivation.

The conjunct polymer can be separated from the silane or borane compound, and the silane or borane compound can be recycled.

The silane or borane reacts with the acid sites of the acidic catalyst. For example, the silane or borane will react with acid sites in a halometallate ionic liquid to form a silyl or boryl halide. The acid sites that were binding the conjunct polymer are no longer present, which allows the conjunct polymer to be removed.

The deactivated acidic catalyst and the silane or borane compound are contacted for a period of time sufficient to allow the acid sites on the conjunct polymer to react with the silane or borane compound. For silane compounds, this will typically take in the range of about 5 sec to about 1 hr, or about 1 min to about 45 min, or about 1 min to about 30 min, or about 1 min to about 15 min. For borane compounds at room temperature, the reaction is slower than with silane compounds, e.g., many hours. The time is less at elevated temperatures, e.g., less than 2 hr at 60° C.

The contacting of the deactivated acidic catalyst and the silane or borane compound typically takes place at a temperature in the range of from about −20° C. to the degradation temperature of the acidic catalyst. For ionic liquids, the upper limit is the decomposition temperature of the ionic liquid. A typical temperature range is about 20° C. to about 80° C. In some embodiments, the contacting takes place at room temperature. In some embodiments with borane compounds, the contacting takes place at temperatures in the range of about 40° C. to about 80° C., or about 70° C.

The pressure is typically ambient pressure, although higher or lower pressures could be used if desired.

In some embodiments, the reaction is conducted under an inert gas so that hydrolysis of the silane or borane does not occur. When the acidic catalyst is an ionic liquid, the ionic liquid may also hydrolyze, so these reactions are desirably conducted under an inert gas. Suitable inert gases include, but are not limited to, nitrogen, helium, neon, argon, krypton, and xenon.

In some embodiments, the volume ratio of the solvent to the deactivated acidic ionic liquid is in a range of about 0.25:1 to about 10:1.

In some embodiments, the molar ratio of the silane compound to the conjunct polymer is in a range of about 1:1 to about 5:1, or about 2:1 to about 3:1. In some embodiments, the molar ratio of the borane compound to the conjunct polymer is in a range of about 0.5:1 to about 5:1, or about 2:1 to about 3:1. In some embodiments, the silane or borane compound can be present in excess of the amount needed for reaction with the conjunct polymer, and the excess silane or borane compound can act as a solvent. In these cases, the molar ratio of the silane or borane compound to the conjunct polymer is more than 5:1, e.g., in the range of 10:1 to about 1000:1.

The contacting can take place in any suitable process, such as solvent extraction, or contacting in one or more mixer/settlers.

The reaction will proceed simply by contacting the silane or borane compound with the liquid acidic catalyst. When a liquid catalyst is used, the reaction rate is generally too slow under static conditions to be commercially viable. When mass transfer rate is controlling, the reaction rate can be substantially increased by increasing the mixing intensity of silane or borane compound and liquid catalyst. After a certain point, increasing the mixing intensity will not provide any additional benefit. Mixing intensity can be controlled using pumps, nozzles, impellers, flow configurations, and baffles. Baffles help to prevent a vortex from forming in the reactor, which would reduce the amount of mixing.

The contacting step of deactivated acidic catalyst and the silane or borane compound may be practiced in laboratory scale experiments through full scale commercial operations. The process may be operated in batch, continuous, or semi-continuous mode. The contacting step can take place in various ways, with both countercurrent and co-current flow processes being suitable. The order of addition of the reactants is not critical. For example, the reactants can be added individually, or some reactants may be combined or mixed before being combined or mixed with other reactants.

After contacting the acidic catalyst and the silane or borane compound, two phases result, a catalyst phase containing the acidic catalyst and an organic phase containing the conjunct polymer and the silyl or boryl compound and solvent, if present. In some embodiments, the phases will separate due to the density difference between the catalyst and the hydrocarbons. In other embodiments, other separation processes may be needed. In some embodiments, the conjunct polymer can be decanted away. Decanting can be suitable if there is enough conjunct polymer present and it separates from the acidic catalyst.

When the acidic catalyst is an ionic liquid, the ionic liquid can be reactivated by adding an appropriate acid. The reactivated acidic catalyst can then be recycled to the hydrocarbon conversion process. Other acidic catalysts may also need to be reactivated by adding an appropriate acid.

The organic phase containing the conjunct polymer and the silyl or boryl compound can be treated as well. The conjunct polymer can be separated from the silyl or boryl compound, and the silyl or boryl compound can be regenerated. The regenerated silane or borane can be recycled and reused to contact with the deactivated acidic catalyst.

The silyl or boryl compound can be chemically reduced to regenerate the silane or borane compound. One method of regeneration is reaction with one or more compounds containing hydrogen, such as one or more metal hydrides. The reaction can take place in a suitable solvent, such as tetrahydrofuran (THF) or toluene. The silyl or boryl compound is converted back to the silane or borane compound and a metal salt byproduct. Suitable metal hydrides include, but are not limited to, LiH, NaH, $CaH_2$, $NaAlH_4$, $LiAlH_4$, KH, $NaBH_4$, diisobutylaluminum hydride, and the like.

The silane or borane regeneration reaction can take place in a few hours at temperatures in the range of about 25° C. to about 70° C., depending on the metal hydride and solvent used.

When the silane or borane compound is mixed with a solvent for the contacting step, the solvent can be recovered before or after separating the conjunct polymer from the silyl or boryl compound. The recovered solvent can be recycled and reused in the process.

In some embodiments, the conjunct polymer is separated from the solvent and silyl or boryl compound at the same time. The separation can take place in a fractionation column, for example. The conjunct polymer may also be adsorbed onto a solid adsorbent such as alumina or activated carbon, and later removed by combustion for heat recovery.

Alternatively, if the solvent is compatible with the subsequent reaction regenerating the silane or borane, the solvent may not be removed. In those situations, the conjunct polymer is separated from the solvent and silyl or boryl compound mixture, and the silyl or boryl compound is regenerated while in the solvent. The solvent and regenerated silane or borane can then be recycled and reused.

In some embodiments, the separation of the conjunct polymer from the silyl or boryl compound may not be complete because the silyl or boryl compound may co-boil with the lower molecular weight conjunct polymer making complete removal difficult.

The regenerated silane or borane can be separated from the metal salt byproduct and recycled back for use in the process. Suitable separation processes include, but are not limited to, filtration, distillation, and decantation.

In another embodiment, the acidic catalyst containing conjunct polymer is passed through a resin containing silane or borane moieties. Suitable resins include, but are not limited to, polystyrene and polyester. The silane or borane moieties react with the acid sites, and the conjunct polymer can be extracted into an organic phase. The ionic liquid is reactivated by adding acid.

In one embodiment, the regeneration process is a solvent extraction process. For ease of discussion, the use of deactivated acidic ionic liquid in the solvent extraction process will be described. However, as will be understood by those of skill in the art, other acidic catalysts which form conjunct polymers could also be used.

In the solvent extraction method, a solvent and a silane or borane compound are added to the ionic liquid containing conjunct polymer. The solvent and the silane or borane compound can be pre-mixed and added together, or they can be added separately, either at the same time or sequentially. Solvent is not always necessary, but it will maximize recovery, removal, and separation of the conjunct polymer.

The silane or borane compound reacts with the free acid and acid sites associated with the conjunct polymer. After these acid sites are quenched, the conjunct polymer migrates from the ionic liquid phase to the organic phase and can be extracted.

In a system without stirring or after stirring is ended, the components can separate into two phases based on the density difference between the ionic liquid phase and the organic phase which contains the conjunct polymer. The ionic liquid will settle to the bottom, and the silane or borane and conjunct polymer will be on top of the ionic liquid layer. Increasing the top layer with additional solvent will increase conjunct polymer recovery.

The deactivated ionic liquid, the solvent, and the silane or borane compound are contacted long enough for the acid sites on the conjunct polymer to react with the silane or borane compound, typically about 5 sec to about 1 hr. The deactivated ionic liquid, the solvent, and the silane or borane compound are typically mixed while being contacted.

The deactivated ionic liquid, the solvent, and the silane or borane compound are typically contacted at a temperature in the range of from about −20° C. to less than the decomposition temperature of the ionic liquid, or about 20° C. to about 80° C. In some embodiments, the contacting takes place at room temperature.

The mixture is then allowed to separate into two phases: an ionic liquid phase and a hydrocarbon phase. The hydrocarbon phase contains the silyl compound, and unreacted silane compound, conjunct polymer, and the solvent. In some embodiments, separation occurs due to the density difference between the ionic liquid phase and the hydrocarbon phase. Separation typically takes on the order of a few minutes to hours; it is generally less than about 1 hr.

The solvent layer is decanted from the ionic liquid. The ionic liquid can be further washed with solvent (either the same solvent used in the extraction or a different one), if desired. As the reaction occurs, the conjunct polymer is extracted into the solvent layer. Volatiles are removed from the organic layer to isolate the conjunct polymer as a viscous oil. In one embodiment, the volatiles can be removed by heating the material under reduced pressure.

In some embodiments, the addition of an acid or an acid precursor reactivates the ionic liquid following removal of the conjunct polymer. Suitable acids and acid precursors include, but are not limited to, HCl, tert-butyl chloride, or 2-chlorobutane. The acid precursor can be any molecule that will break down to form the acid. Reactivation of the ionic liquid with acid or acid precursor typically takes about 5 sec to about 30 min. It can be done at a range of temperatures. For convenience, it is typically done at the same conditions as the hydrocarbon conversion process which generates the conjunct polymer.

The ionic liquid containing the conjunct polymer can be pre-treated before it is contacted with the silane or borane compound. The pretreatment can be used to remove any free acid, such as HCl, which might increase the consumption of the silane or borane compound, and/or any dissolved solvent, which might associate with the conjunct polymer. The pretreatment can be in a fractionation column, for example.

The ionic liquid can be any acidic ionic liquid. There can be one or more ionic liquids. The ionic liquid comprises an organic cation and an anion. Suitable cations include, but are not limited to, nitrogen-containing cations and phosphorus-containing cations. Suitable organic cations include, but are not limited to:

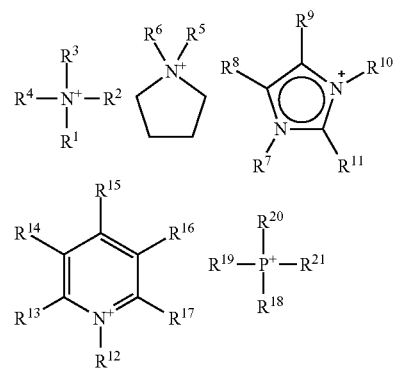

where $R^1$-$R^{21}$ are independently selected from $C_1$-$C_{20}$ hydrocarbons, $C_1$-$C_{20}$ hydrocarbon derivatives, halogens, and H. Suitable hydrocarbons and hydrocarbon derivatives include saturated and unsaturated hydrocarbons, halogen substituted and partially substituted hydrocarbons and mixtures thereof. $C_1$-$C_8$ hydrocarbons are particularly suitable.

The anion can be derived from halides, typically halometallates, and combinations thereof. The anion is typically derived from metal and nonmetal halides, such as metal and nonmetal chlorides, bromides, iodides, fluorides, or combinations thereof. Combinations of halides include, but are not limited to, mixtures of two or more metal or nonmetal halides (e.g., $AlCl_4^-$ and $BF_4^-$), and mixtures of two or more halides with a single metal or nonmetal (e.g., $AlCl_3Br^-$). In some embodiments, the metal is aluminum, with the mole fraction of aluminum ranging from 0<Al<0.25 in the anion. Suitable anions include, but are not limited to, $AlCl_4^-$, $Al_2Cl_7^-$, $Al_3Cl_{10}^-$, $AlCl_3Br^-$, $Al_2Cl_6Br^-$, $Al_3Cl_9Br^-$, $AlBr_4^-$, $Al_2Br_7^-$, $Al_3Br_{10}^-$, $GaCl_4^-$, $Ga_2Cl_7^-$, $GaCl_3Br^-$, $Ga_2Cl_6Br^-$, $Ga_3Cl_9Br^-$, $CuCl_2^-$, $Cu_2Cl_3^-$, $Cu_3Cl_4^-$, $ZnCl_3^-$, $FeCl_3^-$, $FeCl_4^-$, $Fe_3Cl_7^-$, $PF_6^-$, and $BF_4^-$.

The silane compound can be any compound with a reactive SiH moiety. In some embodiments, the silane compound is an organosilane. There can be one or more silanes. Suitable silane compounds include, but are not limited to, silanes having the formulas: $R_3SiH$, $R_2SiH_2$, $RSiH_3$, or $SiH_4$ where each R is independently selected from hydrocarbons or halides. Examples of suitable silanes include triethylsilane, trimethylsilane, triisopropylsilane, and the like. In some embodiments, the silane can be a silane-containing resin.

The silyl compound will be the reaction product of the silane compound and the acid site on the conjunct polymer. When the silane has one of the formulas above, the silyl compound will have the formula: $R_3SiX$, $R_2SiX_2$, $RSiX_3$, or $SiX_4$, where each R is independently selected from hydrocarbons, and each X is independently selected from halides.

The borane compound can be any borane compound having a reactive B—H bond. In some embodiments, the borane compound is an organoborane. There can be one or more boranes. Suitable borane compounds include, but are not limited to, boranes having the formulas: $R_2BH$ or where each R is independently selected from hydrocarbons or halides, or $B_2H_6$, or combinations thereof. Examples of suitable boranes include 9-borabicyclo(3,3,1)nonane, trimesitylborane, trisec-butylborane, diborane, and the like. In some embodiments, the borane can be a borane-containing resin.

The boryl compound will be the reaction product of the borane compound and the acid site on the conjunct polymer. When the borane has the formula $B_2H_6$, the boryl compound will have the formula: $R_2BX$, where each R is independently selected from hydrocarbons or halides. When the borane has the formula $B_2H_6$, the boryl compound is a boron halide compound.

The solvent will depend on the acidic catalyst being regenerated. The solvent can be any solvent which is capable of forming a separate phase from the catalyst phase. There can be one or more solvents. Suitable solvents for halometallate ionic liquids include, but are not limited to, n-paraffins, isoparaffins, and cyclic paraffins, such as $C_4$ to $C_{10}$ paraffins, and aromatic solvents. If the ionic liquid is soluble in hydrocarbons, more polar solvents which are not miscible in the ionic liquid would be used. The use of organic solvents may be less desirable with oxidizing acids.

Alkylation is typically used to combine light olefins, for example mixtures of alkenes such as propylene and butylene, with isobutane to produce a relatively high-octane branched-chain paraffinic hydrocarbon fuel, including isoheptane and isooctane. Similarly, an alkylation reaction can be performed using an aromatic compound such as benzene in place of the isobutane. When alkylating benzene with methylene or ethylene, the product resulting from the alkylation reaction is an alkylbenzene (e.g. toluene, xylenes, ethylbenzene, etc.). For isobutene alkylation, typically, the reactants are mixed in the presence of a strong acid catalyst, such as sulfuric acid or hydrofluoric acid. The alkylation reaction is carried out at mild temperatures, and is typically a two-phase reaction. Because the reaction is exothermic, cooling is needed. Depending on the catalyst used, normal refinery cooling water provides sufficient cooling. Alternatively, a chilled cooling medium can be provided to cool the reaction. The catalyst protonates the alkenes to produce reactive carbocations which alkylate the isobutane reactant, thus forming branched chain paraffins from isobutane. Aromatic alkylation is generally now conducted with solid acid catalysts including zeolites or amorphous silica-aluminas.

The alkylation reaction zone is maintained at a pressure sufficient to maintain the reactants in liquid phase. For a hydrofluoric acid catalyst, a general range of operating pressures is from about 200 to about 7100 kPa absolute. The temperature range covered by this set of conditions is from about −20° C. to about 200° C. For at least alkylation of aromatic compounds, the volumetric ratio of hydrofluoric acid to the total amount of hydrocarbons entering the reactor should be maintained within the broad range of from about 0.2:1 to about 10:1, preferably from about 0.5:1 to about 2:1

Any suitable alkylation catalyst may be used. Typically, the catalysts are acidic. Suitable alkylation catalysts include, but are not limited to, hydrofluoric acid, sulfuric acid, and acidic ionic liquids. Other catalysts include zeolites having a zeolite framework type selected from the groups consisting of beta, MOR, MWW, FAU, and NES. Suitable zeolites include mordenite, ZSM-4, ZSM-12, ZSM-20, offretite, gmelinite, beta, NU-87, UZM-8, MCM-22, MCM-36, MCM-49, zeolite Y, zeolite X, and gottardite. Another class of acidic, solid catalysts are acidified refractory oxides such as chlorided, fluorided, or sulfated alumina, gallia, boria, molybdia, ytterbia, titania, chromia, silica, zirconia, and the like and combinations thereof. Clays and amorphous catalysts may also find utility. Further discussion of alkylation catalysts can be found in U.S. Pat. Nos. 5,196,574; 6,315,964B1 and 6,617,481B1. Newer alkylation catalysts can also be used in this process. For example, one such catalyst comprises a mixture of two types of zeolitic materials, where the zeolites are mixed and produced to have two zeolites within a single catalyst pellet, e.g., UZM-8 and a rare earth substituted X zeolite, Y zeolite, or a zeolite having an EMT/FAU intergrowth.

When ionic liquid catalysts are used for the alkylation, typical alkylation reaction conditions include a temperature in the range of about −20° C. to about 100° C., or about −20° C. to about 70° C., or about 0° C. to about 70° C., or about 20° C. to about 70° C., or about 0° C. to about 60° C., or about 0° C. to about 50° C., or about 20° C. to about 60° C., or about 20° C. to about 50° C. It is preferred to have an ionic liquid that maintains its liquid state through the operating temperature range.

The pressure is typically in the range of atmospheric (0.1 MPa(g)) to about 8.0 MPa(g), or about 0.3 MPa(g) to about 2.5 MPa(g). The pressure is preferably sufficient to keep the reactants in the liquid phase.

The residence time of the reactants in the reaction zone is in the range of a few seconds to hours, or about 0.5 min to about 60 min, or about 5 min to about 60 min.

Processes for the oligomerization of light olefins (e.g. ethylene, propylene, and butylene) to produce higher carbon number olefin products (e.g. $C_{6+}$ olefins) are well known. Oligomerization processes have been employed to produce high quality motor fuel components as well as petrochemicals from ethylene, propylene, and butylene. These oligomerization processes are also referred to as catalytic condensation and polymerization, with the resulting motor fuel often referred to as polymer gasoline. In the refining area, methods have been continually sought to improve the octane number of the gasoline boiling range oligomerization products. This octane enhancement is generally realized through the improvement of the oligomerization reaction selectivity to enhance the representation of high octane blending components (e.g. branched olefins) in the product slate. The ability of the process to better target specific carbon number species is also a primary consideration when highly purified chemical grade products are desired. In any case, the enrichment of product slate to the targeted species, in addition to providing a higher quality and quantity of useable products, also benefits catalyst life. This is due to the reduction in non-selective heavy oligomers that condense into coke which ultimately covers the catalyst.

Known catalysts for effecting the oligomerization reaction include heterogeneous catalysts such as solid acids and homogeneous catalysts, in particular boron trifluoride as described, for example, in U.S. Pat. No. 3,981,941. Other catalysts fall within the description of mild protonic acids, generally having a Hammett acidity function of less than −5.0. Particularly preferred among these are solid phosphoric acid (SPA) catalysts having as a principal ingredient an acid of phosphorous such as ortho, pyro, or tetraphosphoric acid. Details of SPA catalysts are provided in the prior art, for example in U.S. Pat. No. 5,895,830. The use of zeolites as oligomerization catalysts is also described, along with various catalyst treatment methods designed to improve performance in U.S. Pat. Nos. 4,547,613, 4,520,221, 4,642,404, and 5,284,989, for example. Another type of catalyst which may be employed comprises a supported metal compound, as described in U.S. Pat. Nos. 3,562,351, 3,483,269, 3,592,869 3,644,564, 3,679,772, 3,697,617, 3,663,451, 3,755,490, 3,954,668, 3,170,904, 3,170,906. Unsupported metal catalysts are described in Japanese Patent 5024282, Japanese Patent 4722206, U.S. Pat. Nos. 3,155,642, 3,155,642, 3,457, 321, 3,483,268, and 3,505,425, and British Patent 1,123,474. U.S. Pat. No. 4,757,042 describes a catalyst comprising a complex of nickel or palladium, certain fluoro-organo sulfur ligands and an organo-metallic reducing agent.

Oligomerization reaction zones in general are maintained at conditions that may vary widely. The temperature of the oligomerization reaction zones of the present invention in which a resin catalyst is used is typically about −20° C. to about 250° C., or 50° C. to about 150° C., or 50° C. to about 150° C. Pressures in the oligomerization zone using the resin catalyst will be sufficient to maintain the liquid phase in and out of the reactor, typically about 0.3 MPa(g) to about 6.9 MPa(g) (50 to 1000 psig), or about 0.3 MPa(g) to about 3.4 MPa(g) (50 to 500 psig), or about 1.4 MPa(g) to about 2.4 MPa (200 to 350 psig), or about 2.4 MPa(g) to about 6.9 MPa(g) (350 to 1000 psig). Oligomerization conditions may also include a liquid hourly space velocity (LHSV) of about 0.5 to about 8 $hr^{-1}$, or about 1 to about 6 $hr^{-1}$.

Isomerization processes have been used to improve the low octane numbers (RON) of light straight run naphtha. Isomerization processes involve reacting one mole of a hydrocarbon (e.g., normal pentane) to form one mole of an isomer of that specific hydrocarbon (e.g., isopentane). The total number of moles remains the same throughout this process, and the product has the same number of carbons as the reactant.

Current isomerization processes use chlorided alumina, sulfated zirconia, or zeolites in conjunction with platinum. Process temperatures range from about 120° C. for chlorided alumina up to about 260° C. for zeolite type catalysts. These reactions are run at temperatures which allow the feed to reach equilibrium. At lower temperatures, the equilibrium favors the branched isomers possessing the higher octane number.

Isomerization processes utilizing ionic liquids have been developed, such as, US 2003/019767, US 2004/059173, U.S. Pat. No. 7,053,261, for example. Isomerization processes utilizing ionic liquid catalysts were described in application Ser. No. 13/931,765, entitled CATALYTIC ISOMERIZATION OF PARAFFINS USING IONIC LIQUID, filed Jun. 28, 2013; application Ser. No. 13/931,770, entitled CATALYTIC ISOMERIZATION OF HEPTANE USING IONIC LIQUID, filed Jun. 28, 2013; application Ser. No. 13/931, 776, entitled CATALYTIC ISOMERIZATION OF PENTANE USING IONIC LIQUID, filed Jun. 28, 2013; each of which is incorporated herein by reference.

Suitable reaction conditions for processes using ionic liquids include a temperature of less than the decomposition temperature of the ionic liquid, or about 250° C. or less, or about 200° C. or less, or about 175° C. or less, or about 150° C. or less, or about 125° C. or less, or about 100° C. or less, or about 90° C. or less, or about 80° C. or less, or about 70° C. or less, or about 60° C. or less, or in the range of about 0° C. to about 200° C., or about 0° C. to about 175° C., or about 0° C. to about 150° C., or about 10° C. to about 150° C., or about 25° C. to about 150° C., or about 30° C. to about 150° C., or about 40° C. to about 150° C., or about 50° C. to about 150° C., or about 55° C. to about 150° C.

The pressure in the reaction zone is typically in the range of about 0 MPa to about 13.8 MPa, or about 0 MPa to about 8.1 MPa, or about 0 MPa to about 5 MPa, or about 0 MPa to about 3.5 MPa. The pressure should be sufficient to ensure that the reaction product is in a liquid state. Small amounts of vapor may also be present, but this should be minimized.

The reaction can take place in the presence of a gas. Suitable gases include, but are not limited to methane, ethane, propane, hydrogen, hydrogen chloride, nitrogen and the like.

The residence time in the reaction zone is generally less than about 12 hr, or less than about 10 hr, or less than 7 hr, or less than 5 hr, or less than 4 hr, or less than 3 hr, or less than 2 hr, or less than 1 hr. The reaction time can be selected so that a predetermined conversion can be obtained. When the catalyst is an ionic liquid, the reaction time is a function of the degree of mixing, the reaction temperature, and the mass/volume ratio of liquid catalyst to hydrocarbon being reacted. Generally, increasing any of these conditions will increase the reaction rate.

The disproportionation of paraffins (e.g., isopentane ($iC_5$)) involves reacting two moles of hydrocarbon to form one mole each of two different products, one having a carbon count greater than the starting material and the other having a carbon count less than the starting material. The total number of moles in the system remains the same throughout the process, but the products have different carbon counts from the reactants.

Suitable reaction conditions include a temperature of less than the decomposition temperature of the ionic liquid, or about 250° C. or less, or about 200° C. or less, or about 175° C. or less, or about 150° C. or less, or about 125° C. or less, or about 100° C. or less, or about 90° C. or less, or about 80° C. or less, or about 70° C. or less, or about 60° C. or less, or in the range of about 0° C. to about 200° C., or about 0° C. to about 175° C., or about 0° C. to about 150° C., or about 10° C. to about 150° C., or about 25° C. to about 150° C., or about 30° C. to about 150° C., or about 40° C. to about 150° C., or about 50° C. to about 150° C., or about 55° C. to about 150° C.

The pressure in the reaction zone is typically in the range of about 0 MPa to about 13.8 MPa, or about 0 MPa to about 8.1 MPa, or about 0 MPa to about 5 MPa, or about 0 MPa to about 3.5 MPa. The pressure should be sufficient to ensure that the reaction product is in a liquid state. Small amounts of vapor may also be present, but this should be minimized.

The reaction can take place in the presence of a gas. Suitable gases include, but are not limited to methane, ethane, propane, hydrogen, hydrogen chloride, nitrogen and the like.

The residence time in the reaction zone is generally less than about 12 hr, or less than about 10 hr, or less than 7 hr, or less than 5 hr, or less than 4 hr, or less than 3 hr, or less than 2 hr, or less than 1 hr. The reaction time can be selected so that a predetermined conversion can be obtained.

Suitable catalysts include, but are not limited to, HF, sulfated zirconias, $AlCl_2/SiO_2$, zeolites, ionic solids, platinum on chlorided $Al_2O_3/Ga_2O_3$ supports, supported ionic liquids, $Pt/W/Al_2O_3$, $HF/TiF_4$, ionic liquids, or combinations thereof. The first and second catalysts can be the same or different.

Disproportionation processes using ionic liquids were described in application Ser. No. 13/931,780, entitled CATALYTIC DISPROPORTIONATION OF PARAFFINS USING IONIC LIQUID, filed Jun. 28, 2013; application Ser. No.

13/931,783, entitled CATALYTIC DISPROPORTIONATION OF HEPTANE USING IONIC LIQUID, filed Jun. 28, 2013; and application Ser. No. 13/931,789, entitled CATALYTIC DISPROPORTIONATION OF PENTANE USING IONIC LIQUID, filed Jun. 28, 2013; each of which is incorporated herein by reference.

The microscopic reverse of pentane disproportionation is the combination of one mole of hexane and one mole of butane to form two moles of pentane. This type of reaction is referred to herein as reverse disproportionation. Reverse disproportionation-type reactions can occur in which two paraffins having different carbon numbers react to form two different paraffins having different carbon numbers from those of the feed where the total number of moles of product and moles of carbon and hydrogen in the products does not change from the total number in the feed (e.g., pentane and octane reacting to form hexane and heptane). These reactions are sometimes referred to as comproportionation or molecular averaging reactions. These paraffin rearrangements have also been called alkane metathesis. The use of any of these terms is meant to illustrate that paraffins can react with other paraffins to form additional paraffins different from the original feed. Utilizing the equilibrium among the various species, the concentration of the product can be controlled by varying the relative ratios of the species. Consequently, two different paraffinic feed sources of varying carbon count can be reacted to obtain a product containing paraffins of intermediate carbon count.

Suitable hydrocarbon feed for reverse disproportionation reactions includes one larger and one smaller paraffin feed to produce a product composition having an intermediate carbon count. The smaller feed typically has carbon numbers ranging from 4-23, and the larger feed typically has carbon numbers ranging from 6-25. There is generally a difference of at least 2 or more carbon numbers between the two feeds, or at least 3, or at least 4, or at least 5, or at least 6 or more.

The liquid hydrocarbon feed is contacted with the liquid catalyst at temperatures of less than the decomposition temperature of the ionic liquid, or about 250° C. or less, or about 200° C. or less, or about 175° C. or less, or about 150° C. or less, or about 125° C. or less, or about 100° C. or less, or about 90° C. or less, or about 80° C. or less, or about 70° C. or less, or about 60° C. or less, or in the range of about 0° C. to about 200° C., or about 0° C. to about 175° C., or about 0° C. to about 150° C., or about 10° C. to about 150° C., or about 25° C. to about 150° C., or about 30° C. to about 150° C., or about 40° C. to about 150° C., or about 50° C. to about 150° C., or about 55° C. to about 150° C.

The pressure in the reaction zone is typically in the range of about 0 MPa to about 13.8 MPa. The pressure should be sufficient to ensure that the hydrocarbon feed is in a liquid state. Small amounts of vapor may also be present, but this should be minimized.

The reaction typically takes places in the presence of a gas. Suitable gases include, but are not limited to nitrogen, hydrogen, argon, helium, hydrogen chloride and the like.

The residence time in the reaction zone is generally less than about 10 hr, or less than 7 hr, or less than 5 hr, or less than 4 hr, or less than 3 hr, or less than 2 hr, or less than 1 hr.

Reverse disproportionation processes using ionic liquids were described in Application Ser. No. 61/841,263, entitled CATALYTIC REVERSE DISPROPORTIONATION OF PARAFFINS USING IONIC LIQUID, filed Jun. 28, 2013, which is incorporated herein by reference.

The FIGURE illustrates one embodiment of a hydrocarbon conversion process 100, such as alkylation, oligomerization, isomerization, disproportionation, and the like. For ease of discussion, the process will be described for use in an alkylation process using tributylhexylphosphonium chloroaluminate ionic liquid (TBHP-Al$_2$Cl$_7$), triethylsilane (TESi-H), and n-butane (nC$_4$) solvent. Other acidic catalysts, (including other acidic ionic liquids), silane or borane compounds, and solvents could also be used, as would be understood by those skilled in the art.

The hydrocarbon feed 105 containing butanes and butenes is sent to alkylation reaction zone 110. An ionic liquid catalyst stream 115 is also introduced into the alkylation reaction zone 110. The butenes are alkylated in the alkylation reaction zone 110 resulting in a hydrocarbon phase containing the alkylated product and an ionic liquid phase. Over time, the ionic liquid phase will contain conjunct polymer as a result of the alkylation process. As the amount of conjunct polymer increases, the ionic liquid becomes deactivated.

The reaction mixture 120 from the alkylation reaction zone 110 is sent to a separation zone 125 where the hydrocarbon phase 130 is separated from the ionic liquid phase 135. The separation can occur based on the density difference between the hydrocarbon phase 130 and the ionic liquid phase 135.

The hydrocarbon phase 130 is sent to a separation zone 140 where it is separated into at least an alkylate product stream 145 and an isobutane stream 150. The alkylate stream is recovered and used in a gasoline product, for example. The isobutane stream 150 can be recycled to the alkylation reaction zone 110.

At least a portion 155 of the ionic liquid phase 135 is sent to the reactive extraction zone 165. In some embodiments, all of the ionic liquid phase 135 is sent to the reactive extraction zone 165. In some embodiments, a portion 160 of the ionic liquid phase 135 from the separation zone 125 is recycled to the alkylation reaction zone 110.

The portion 155 of the ionic liquid phase 135 is introduced into the reactive extraction zone 165. The ionic liquid is TBHP-Al$_2$Cl$_7$. The portion 155 of the ionic liquid phase 135 which contains conjunct polymer contains

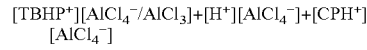

where [CPH$^+$] represents the protonated conjunct polymer.

A known amount of silane compound 170 is introduced into the reactive extraction zone 165. In some embodiments, a solvent stream 175 is also introduced into the reactive extraction zone 165. If present, the solvent stream 175 can be introduced separately, or mixed with the silane compound 170 prior to being introduced.

The silane compound 170 and the solvent stream 175 contain

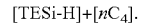

The portion 155 of the ionic liquid phase 135 containing the conjunct polymer reacts with the TESi-H to form triethylsilylchloride (TESi-Cl). Although not wishing to be bound by theory, it is believed that a reaction occurs between the TESi-H and the acid sites associated with the conjunct polymers. When the conjunct polymer is no longer protonated, it becomes an organic-like molecule (no longer charged), so it is easily transferred to the organic phase.

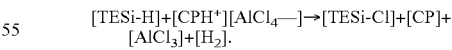

The ionic liquid phase with the conjunct polymer removed 180 can be separated from the hydrocarbon phase 185 by taking advantage of the fact that it has a higher density than the hydrocarbon phase 185.

The ionic liquid phase 180 contains dissolved/suspended AlCl$_3$, which is reactivated by adding an acid 190, such as HCl, in zone 195 to restore the active acid site:

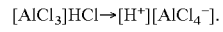

The re-activated ionic liquid 200 contains

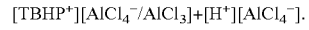

Fresh ionic liquid 205 can be added to the reactivated ionic liquid 200, if needed, and the re-activated ionic liquid 200 can be recycled back to the alkylation reaction zone 110 as ionic liquid catalyst stream 115.

The hydrocarbon phase 185 contains the TESi-Cl, solvent, conjunct polymer, hydrogen, and any unreacted TESi-H.

[TESi-Cl]+[nC$_4$]+[CP]+[H$_2$]+[TESi-H].

The TESi-Cl in the hydrocarbon phase 185 is reacted to regenerate the TESi-H in a reaction zone 215. One method of regenerating the TESi-Cl is with reducing agents that contain H$^-$, such as metal hydrides. The metal hydride 220 is added to reaction zone 215. A second solvent 225 is also added.

[TESi-Cl]+MH→[TESi-H]+[MCl].

The metal salt 235 is removed from reaction zone 215. The effluent 230 from the reaction zone 215 contains the regenerated TESi-H, the solvent, and the conjunct polymer.

[TESi-H]+[nC$_4$]+[CP].

The effluent 230 from the reaction zone 215 can be sent to a separation zone 240 where the solvent and TESi-H 245 are separated from the conjunct polymer 250. The solvent and TESi-H stream 245 from separation zone 240 can be recycled to the reactive extraction zone 165. The second solvent goes through the process and is recycled with the TESi-H to the reactive extraction zone 165 in stream 245.

EXAMPLES

Preparation of Spent Ionic Liquid

The spent ionic liquid samples were generated in a continuous alkylation process in which 2-butenes were contacted with tributylhexylphosphonium heptachloroaluminate ionic liquid in the presence of isobutane and 2-chlorobutane. Contacting took place in a stirred 300 mL autoclave stirred at 1200 rpm. The mixture was continuously transferred to a gravity separator and the IL recycled to the alkylation reactor. Flow rates and feed ratios varied over the course of the reaction which took place over several days to weeks for the various samples. At the end of each run, the heavy fraction containing ionic liquid was collected and stored under nitrogen. The % CP in each of the spent samples was determined by extraction and isolation of CP. The spent ionic liquid was mixed with water. The CP was extracted from the IL/water mixture with hexane. The hexane was removed on a rotary evaporator and the mass of the isolated CP was determined.

Examples 1-6

Under a nitrogen atmosphere, 4 g of spent TBHP-Al$_2$Cl$_7$ IL containing 10.42% wt conjunct polymer was added to a glass vial equipped with a stir bar, followed by the required amount of anhydrous nC$_8$ to obtain a 0.86 vol ratio of nC$_8$ to IL. The amount of triethylsilane was varied, as shown in Table 1. Stirring was initiated and continued for 15 minutes at room temperature. Stirring was then stopped, and the phases were allowed to separate. The hydrocarbon phase was analyzed by either GC or $^{29}$Si NMR to determine the extent of triethylsilane conversion. The resulting IL was hydrolyzed, and the extent of residual conjunct polymer was determined by extracting with hydrocarbon and further solvent removal under reduced pressure. The extent of CP removal ranged from 60-95% wt. Increasing the triethylsilane to CP mol ratio improved the extent of CP removal. The results are shown in Table 1.

TABLE 1

Impact of TES:CP mol ratio on % CP Removal. Experiments conducted with 4 g of spent IL, at 0.86 volume ratio of nC$_8$ to IL, 25° C., for 15 minutes.

| Experiment | % CP in IL | TES:CP mol ratio added | % CP Removed | TESi:CP mol ratio converted |
|---|---|---|---|---|
| Example 1 | 10.42% | 1.63 | 66% | 1.63 |
| Example 2 |  | 1.83 | 60% | 1.80 |
| Example 3 |  | 2.01 | 74% | 2.01 |
| Example 4 |  | 2.49 | 95% | 2.44 |
| Example 5 |  | 2.71 | 85% | 2.49 |
| Example 6 |  | 2.90 | 86% | 2.60 |

Example 7

Under a nitrogen atmosphere, 50 g of spent TBHP-Al$_2$Cl$_7$ IL containing 10.99% wt conjunct polymer was added to a flask equipped with a stir bar, followed by the required amount of anhydrous nC$_6$ to obtain the indicated solvent to IL ratio. The appropriate amount of triethylsilane was added to obtain the indicated ratio of triethylsilane to conjunct polymer. Stirring was initiated and continued for 15 minutes at room temperature. Stirring was then stopped, and the phases were allowed to separate. The hydrocarbon phase was analyzed by either GC or $^{29}$Si NMR to determine the extent of triethylsilane conversion. The resulting IL was hydrolyzed, and the extent of residual conjunct polymer was determined by extracting with hydrocarbon and further solvent removal under reduced pressure. The extent of CP removal was determined to be 68% wt. The results are shown in Table 2.

Example 8

Under a nitrogen atmosphere, 4 g of spent TBHP-Al$_2$Cl$_7$ IL containing 10.42% wt conjunct polymer was added to a glass vial equipped with a stir bar, followed by the required amount of anhydrous nC$_8$. The appropriate amount of triethylsilane was added. Stirring was initiated and continued for 15 minutes at room temperature. Stirring was then stopped, and the phases were allowed to separate. The hydrocarbon phase was analyzed by either GC or $^{29}$Si NMR to determine the extent of triethylsilane conversion. The resulting IL was hydrolyzed, and the extent of residual conjunct polymer was determined by extracting with hydrocarbon and further solvent removal under reduced pressure. The % wt CP removal was determined to be 74%. The results are shown in Table 2.

TABLE 2

Impact of hydrocarbon type on % CP Removal. Experiments conducted at 25° C., for 15 minutes.

| Experiment | % CP in IL | TES:CP mol ratio added | g IL | Solvent | Solvent:IL vol ratio | % CP Removed | TESi:CP mol ratio converted |
|---|---|---|---|---|---|---|---|
| Example 7 | 10.99% | 2.13 | 50 | nC6 | 0.39 | 68% | 2.13 |
| Example 8 | 10.42% | 2.01 | 4 | nC8 | 0.55 | 74% | 2.01 |

Examples 9-10

Under a nitrogen atmosphere, 16 g of spent TBHP-Al$_2$Cl$_7$ IL containing 3.04% wt conjunct polymer was added to a flask equipped with a stir bar, followed by the required amount of anhydrous nC$_8$ to obtain the indicated solvent to IL ratio, which was varied as shown in Table 3. The appropriate amount of triethylsilane was added to obtain the indicated ratio of triethylsilane to conjunct polymer. Stirring was initiated and continued for 15 minutes at room temperature. Stirring was then stopped, and the phases were allowed to separate. The hydrocarbon phase was analyzed by either GC or $^{29}$Si NMR to determine the extent of triethylsilane conversion. The resulting IL was hydrolyzed, and the extent of residual conjunct polymer was determined by extracting with hydrocarbon and further solvent removal under reduced pressure. The % wt CP removal was determined to be 64% and 90%, respectively. The results are shown in Table 3.

Examples 11-12

Under a nitrogen atmosphere, 14 g of spent TBHP-Al$_2$Cl$_7$ IL containing 6.82% wt conjunct polymer was added to a flask equipped with a stir bar, followed by the required amount of anhydrous nC$_8$, which was varied as shown in Table 3. The appropriate amount of triethylsilane was added. Stirring was initiated and continued for 15 minutes at room temperature. Stirring was then stopped, and the phases were allowed to separate. The hydrocarbon phase was analyzed by either GC or $^{29}$Si NMR to determine the extent of triethylsilane conversion. The resulting IL was hydrolyzed, and the extent of residual conjunct polymer was determined by extracting with hydrocarbon and further solvent removal under reduced pressure. The % wt CP removal was determined to be 81% and 72%, respectively. The results are shown in Table 3.

Examples 13-16

Under a nitrogen atmosphere, 4 g of spent TBHP-Al$_2$Cl$_7$ IL containing 10.42% wt conjunct polymer was added to a glass vial equipped with a stir bar, followed by the required amount of anhydrous nC$_8$, which was varied as shown in Table 3. The appropriate amount of triethylsilane was added. Stirring was initiated and continued for 15 minutes at room temperature. Stirring was then stopped, and the phases were allowed to separate. The hydrocarbon phase was analyzed by either GC or $^{29}$Si NMR to determine the extent of triethylsilane conversion. The resulting IL was hydrolyzed, and the extent of residual conjunct polymer was determined by extracting with hydrocarbon and further solvent removal under reduced pressure. The % wt CP removal ranged from 74% to 78%. The results are shown in Table 3.

Examples 17-18

Under a nitrogen atmosphere, 4 g of spent TBHP IL containing 14.80% wt conjunct polymer was added to a glass vial equipped with a stir bar, followed by the required amount of anhydrous nC$_8$, which was varied as shown in Table 3. The appropriate amount of triethylsilane was added. Stirring was initiated and continued for 15 minutes at room temperature. Stirring was then stopped, and the phases were allowed to separate. The hydrocarbon phase was analyzed by either GC or $^{29}$Si NMR to determine the extent of triethylsilane conversion. The resulting IL was hydrolyzed, and the extent of residual conjunct polymer was determined by extracting with hydrocarbon and further solvent removal under reduced pressure. The % wt CP removal was determined to be 67% and 76%, respectively. The results are shown in Table 3.

TABLE 3

Impact of hydrocarbon to IL volume ratio on % CP Removal.
Experiments conducted in nC$_8$ at 25° C., for 15 minutes.

| Experiment | % CP in IL | TES:CP mol ratio added | g IL | Solvent:IL vol ratio | % CP Removed | TESi:CP mol ratio converted |
|---|---|---|---|---|---|---|
| Example 9  | 3.04%  | 2.27 | 16.0 | 0.85 | 64% | 2.26 |
| Example 10 |        |      |      | 1.18 | 90% | 2.24 |
| Example 11 | 6.82%  | 2.28 | 14.0 | 0.86 | 81% | 2.28 |
| Example 12 |        |      |      | 1.51 | 72% | 2.20 |
| Example 13 | 10.42% | 2.01 | 4.0  | 0.55 | 74% | 2.01 |
| Example 14 |        |      |      | 0.65 | 77% | 2.00 |
| Example 15 |        |      |      | 0.75 | 78% | 2.01 |
| Example 16 |        |      |      | 0.86 | 74% | 2.01 |
| Example 17 | 14.80% | 2.50 | 4.0  | 0.86 | 67% | 2.50 |
| Example 18 |        |      |      | 1.71 | 76% | 2.49 |

Examples 19-24

Under a nitrogen atmosphere, spent TBHP-Al$_2$Cl$_7$ IL containing 6.82% wt conjunct polymer was added to a flask equipped with a stir bar, followed by the required amount of anhydrous nC$_8$ to obtain a 0.86 vol ratio of nC$_8$ to IL, which was kept constant as shown in Table 4. The appropriate amount of triethylsilane was added to obtain the indicated ratio of triethylsilane to conjunct polymer. Stirring was initiated and continued for 15 minutes at the temperature designated in Table 4. Stirring was then stopped, and the phases were allowed to separate. The hydrocarbon phase was analyzed by either GC or $^{29}$Si NMR to determine the extent of triethylsilane conversion. The resulting IL was hydrolyzed, and the extent of residual conjunct polymer was determined by extracting with hydrocarbon and further solvent removal under reduced pressure. The % wt CP removal ranged from 25% to 80%. The results are shown in Table 4.

TABLE 4

Impact of reaction temperature on % CP Removal.
Experiments conducted in $nC_8$ for 15 minutes.

| Experiment | % CP in IL | TES:CP mol ratio added | g IL | Solvent:IL vol ratio | Temp °C. | % CP Removed | TESi:CP mol ratio converted |
|---|---|---|---|---|---|---|---|
| Example 19 | 6.82% | 1.33 | 14.0 | 0.86 | 25 | 25% | 1.33 |
| Example 20 | | | | | 80 | 42% | 1.38 |
| Example 21 | | 1.77 | 14.0 | | 25 | 37% | 1.54 |
| Example 22 | | | | | 80 | 22% | 1.87 |
| Example 23 | | 2.27 | 14.0 | | 25 | 81% | 2.28 |
| Example 24 | | | 16.0 | | 60 | 82% | 2.27 |

Examples 25-28

Under a nitrogen atmosphere, spent $TBHP-Al_2Cl_7$ IL containing 6.82% wt conjunct polymer was added to a glass vial equipped with a stir bar, followed by the required amount of anhydrous $nC_8$ to obtain a 0.86 vol ratio of $nC_8$ to IL, which was kept constant as shown in Table 5. The appropriate amount of triethylsilane was added to obtain a ratio of triethylsilane to conjunct polymer of 2.03. Stirring was initiated and continued for the specified amount of time as indicated in Table 5, at room temperature. Stirring was then stopped, and the phases were allowed to separate. The hydrocarbon phase was analyzed by either GC or $^{29}Si$ NMR to determine the extent of triethylsilane conversion. The resulting IL was hydrolyzed, and the extent of residual conjunct polymer was determined by extracting with hydrocarbon and further solvent removal under reduced pressure. The % wt CP removal ranged from 49% to 76%. The results are shown in Table 5.

Examples 29-32

Under a nitrogen atmosphere, spent $TBHP-Al_2Cl_7$ IL containing 10.42% wt conjunct polymer was added to a glass vial equipped with a stir bar, followed by the required amount of anhydrous $nC_8$ to obtain a 0.86 vol ratio of $nC_8$ to IL, which was kept constant as shown in Table 5. The appropriate amount of triethylsilane was added to obtain a ratio of triethylsilane to conjunct polymer of 2.03. Stirring was initiated and continued for the specified amount of time as indicated in Table 5, at room temperature. Stirring was then stopped, and the phases were allowed to separate. The hydrocarbon phase was analyzed by either GC or $^{29}Si$ NMR to determine the extent of triethylsilane conversion. The resulting IL was hydrolyzed, and the extent of residual conjunct polymer was determined by extracting with hydrocarbon and further solvent removal under reduced pressure. The % wt CP removal ranged from 55% to 80%. The results are shown in Table 5.

Examples 33-38

FIG. 3 is a graph showing the TESi:CP mol ratio converted as a function of the TESi:CP mol ratio added. For ionic liquids containing conjunct polymer in the range of 0-10%, approximately 2.5 molar equivalents of TESi-H are consumed relative to CP. When excess TESi-H was added to these ionic liquids, the TESi-H was not consumed by secondary reactions and could be recovered in the hydrocarbon phase and recycled back to the regenerator. For batches of ionic liquid containing up to 15% CP, the amount of TESi-H consumed per mole of CP increases to 3.5 molar equivalents.

| Example | Composition - wt % CP |
|---|---|
| 33 | 10.99% |
| 34 | 3.04% |
| 35 | 6.82% |
| 36 | 6.82% |
| 37 | 10.42% |
| 38 | 14.80% |

Examples 39-44

FIG. 4 is a graph showing experiments where more than 95% of the TESi-H was converted. It shows the correlation of CP removal relative to the amount of TESi-H added. In general, the greatest amount of CP can be removed when sufficient amount of TESi-H has been added. For ionic liquids containing up to 10% CP, 2.5 mole equivalents are needed to achieve more than 80% CP removal. For ionic liquids containing up to 15% CP, 3.5 mole equivalents were needed to achieve more than 90% CP removal.

TABLE 5

Impact of reaction time on % CP removal. Experiments conducted at 25° C. in $nC_8$ with a solvent to IL volume ratio of 0.86.

| Experiment | % CP in IL | TES:CP mol ratio added | g IL | Residence Time (min) | % CP Removed | TESi:CP mol ratio converted |
|---|---|---|---|---|---|---|
| Example 25 | 6.82% | 2.03 | 7.0 | 0.25 | 49% | 0.70 |
| Example 26 | | | 7.0 | 1 | 64% | 1.63 |
| Example 27 | | | 2.5 | 3 | 76% | 1.99 |
| Example 28 | | | 4.0 | 13 | 72% | 2.01 |
| Example 29 | 10.42% | | 4.0 | 1 | 55% | 1.46 |
| Example 30 | | | 4.0 | 3 | 63% | 1.79 |
| Example 31 | | | 4.0 | 7 | 80% | 2.04 |
| Example 32 | | | 4.0 | 11 | 80% | 2.00 |

| Example | Composition - wt % CP, solvent:IL (vol) |
|---------|------------------------------------------|
| 39 | 10.99% CP, 0.45 |
| 40 | 6.82% CP, 0.86 |
| 41 | 6.82% CP, 1.5 |
| 42 | 10.42% CP, 0.86 |
| 43 | 14.8% CP, 0.86 |
| 44 | 14.8% CP, 1.7 |

Example 45

Reduction of Chlorotriethyl Silane with LiH

LiH (0.8 g; 0.1 mol) and anhydrous THF solvent (44 g; 0.616 mol) were heated with stirring to 60° C. in the drybox. Commercial grade chlorotriethylsilane (7.54 g; 0.05 mol) was added drop-wise over a span of about 15 minutes. Heating was stopped, but the reaction mixture was allowed to continue stirring at room temperature overnight. The next morning, stirring was stopped, and a liquid aliquot was analyzed by GC after filtration. Conversion of TES-Cl to TES was found to be about 82%. The reaction mixture was heated again for another 2 hours and allowed to stir overnight at room temperature. GC analysis the next morning confirmed complete conversion.

Example 46

Reduction of Chlorotriethyl Silane with NaAlH$_4$

NaAlH$_4$ (1.43 g; 0.0265 mol), tributylhexylphosphonium chloride (0.21 g; 0.00065 mol), and toluene (265 mL) were heated with stirring to 65° C. in the glovebox. Commercial grade chlorotriethylsilane (2.0 g; 0.013 mol) was added drop-wise over the span of about 10 minutes. After 1 hour, heating was stopped, but the reaction mixture was allowed to continue stirring at room temperature overnight. The next morning, stirring was stopped, and a liquid aliquot was analyzed by GC. Conversion of TES-Cl to TES-H was found to be only about 24%. The reaction mixture was heated again for another 4 hours and allowed to stir over the weekend at room temperature. GC analysis then confirmed complete conversion.

Example 47

Reduction of Chlorotriethylsilane in the Presence of CP and Solvent with LiH

In the glovebox, 18 g of spent IL (6.16% wt CP), triethylsilane (0.645 g; 0.0055 mol), and 4 g of nC$_6$ were contacted at room temperature for 15 minutes. An aliquot of the product solution was analyzed by GC showing 69% conversion of TES to TES-Cl. To the organic phase from the reaction above was added anhydrous THF (4.89 g; 0.068 mol) and LiH (0.09 g; 0.011 mol). The reaction stirred at room temperature overnight. The next morning GC analysis showed that only 15% of the TES-Cl had converted to TES. The reaction mixture was heated to 60° C. for 3.5 hours after which complete conversion to TES was obtained.

Example 48

Borane

Spent ionic liquid samples were generated in a continuous alkylation process in which 2-butenes were contacted with tributylhexylphosphonium heptachloroaluminate ionic liquid in the presence of isobutane and 2-chlorobutane. Contacting took place in a stirred 300 mL autoclave stirred at 1200 rpm. The mixture was continuously transferred to a gravity separator and the IL recycled to the alkylation reactor. Flow rates and feed ratios varied over the course of the reaction which took place over several days to weeks for the various samples. At the end of each run, the heavy fraction containing ionic liquid was collected and stored under nitrogen.

Under a nitrogen atmosphere, hexane was added to spent TBHP-Al$_2$Cl$_7$ ionic liquid containing conjunct polymer followed by the addition of 9-BBN as a solution in hexane. After stirring in an autoclave for 1 hr at 70° C., the mixture was allowed to settle to separate the hexane layer and the ionic liquid layer. The hexane layer was decanted from the ionic liquid layer. The ionic liquid layer was further washed with pentane. Upon exposure to air, a white precipitate was formed which was filtered out of the hexane layer. The volatiles were removed from the hexane layer to isolate the conjunct polymer as a viscous oil (92% of the conjunct polymer was isolated). The isolated conjunct polymer is a similar molecular weight to conjunct polymer previously isolated using silane compounds. The addition of 2-chlorobutane to the ionic liquid layer restored the activity of the ionic liquid. The performance was similar to fresh ionic liquid, with a RONC of 95 for the regenerated ionic liquid and a RONC of 94 for the fresh ionic liquid, and with a butene conversion of 99% for both ionic liquids.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

What is claimed is:

1. A hydrocarbon conversion process comprising:
    contacting a hydrocarbon feed with an acidic catalyst under hydrocarbon conversion conditions in a hydrocarbon conversion zone wherein the hydrocarbon conversion is alkylation of aromatics, alkylation of isoparaffins or both, the acidic catalyst selected from the group consisting of sulfuric acid, hydrofluoric acid, trifluoromethanesulfonic acid, phosphoric acid, boron trifluoride, and acidic ionic liquids, the hydrocarbon feed reacting to form a mixture comprising reaction products, the acidic catalyst, and deactivated acidic catalyst containing conjunct polymer;
    separating the mixture into at least two streams, a first stream comprising the reaction products and a second stream comprising the deactivated acidic catalyst containing conjunct polymer;
    recovering the reaction products;
    contacting the deactivated acidic catalyst containing the conjunct polymer with at least one silane or borane compound in a regeneration zone under regeneration conditions, the conjunct polymer reacting with the at least one silane or borane compound resulting in a catalyst phase and an organic phase containing the conjunct polymer and at least one silyl or boryl compound.

2. The process of claim 1 wherein the hydrocarbon conversion conditions include at least one of a temperature in a range of about −20° C. to about 250° C., or a pressure in a range of about 0 MPa to about 13.8 MPa.

3. The process of claim 1 further comprising:
mixing an acid with the catalyst phase to reactivate the acidic catalyst; and
recycling the reactivated acidic catalyst to the hydrocarbon conversion zone.

4. The process of claim 3 further comprising separating the catalyst phase from the organic phase before mixing the acid with the catalyst phase.

5. The process of claim 1 further comprising:
chemically reducing the at least one silyl or boryl compound to regenerate the at least one silane or borane compound.

6. The process of claim 5 further comprising separating the at least one regenerated silane or borane compound from the conjunct polymer.

7. The process of claim 1 wherein contacting the deactivated acidic catalyst containing the conjunct polymer with the at least one silane or borane compound comprises contacting the deactivated acidic catalyst containing the conjunct polymer with the at least one silane or borane compound and a solvent, wherein the solvent is capable of forming a separate phase from the acidic catalyst.

8. The process of claim 7 further comprising:
chemically reducing the at least one silyl or boryl compound to regenerate the at least one silane or borane compound; and
separating the at least one regenerated silane or borane compound and the solvent from the conjunct polymer.

9. The process of claim 7 wherein a volume ratio of the solvent to the deactivated acidic catalyst containing the conjunct polymer is in a range of about 0.25:1 to about 10:1.

10. The process of claim 7 wherein the solvent comprises a normal paraffin, an isoparaffin, or a cyclic paraffin having up to 10 carbon atoms, an aromatic, or the at least one silane or borane compound, or combinations thereof.

11. The process of claim 1 wherein a molar ratio of the at least one silane or borane compound to the conjunct polymer is in a range of about 1:1 to about 5:1.

12. The process of claim 1 wherein the deactivated acidic catalyst containing the conjunct polymer comprises the ionic liquid.

13. The process of claim 12 wherein the regeneration conditions include a temperature in a range of from about −20° C. to less than a decomposition temperature of the ionic liquid.

14. The process of claim 12 further comprising pretreating the deactivated catalyst containing the conjunct polymer before contacting the deactivated acidic catalyst containing the conjunct polymer with the at least one silane or borane compound.

15. The process of claim 1 wherein contacting the deactivated acidic catalyst containing the conjunct polymer with the at least one silane or borane compound further comprises mixing the deactivated acidic catalyst containing the conjunct polymer with the at least one silane or borane compound.

16. The process of claim 1 wherein the deactivated acidic catalyst containing the conjunct polymer is contacted with the at least one silane or borane compound for between about 5 sec and about 1 hr.

17. The process of claim 1 wherein the at least one silane compound has a formula: $R_3SiH$, $R_2SiH_2$, $RSiH_3$, or $SiH_4$, where each R is independently selected from hydrocarbons or halides, or the at least one borane compound comprises a compound having a formula $R_2BH$, where each R is independently selected from hydrocarbons or halides, or $B_2H_6$, or combinations thereof.

18. A hydrocarbon conversion process comprising:
contacting a hydrocarbon feed with an acidic catalyst under hydrocarbon conversion conditions in a hydrocarbon conversion zone wherein the hydrocarbon conversion is alkylation of aromatics, alkylation of isoparaffins, or both, the acidic catalyst selected from the group consisting of sulfuric acid, hydrofluoric acid, trifluoromethanesulfonic acid, phosphoric acid, boron trifluoride, and acidic ionic liquids, the hydrocarbon feed reacting to form a mixture comprising reaction products, the acidic catalyst, and deactivated acidic catalyst containing conjunct polymer;
separating the mixture into at least two streams, a first stream comprising the reaction products and a second stream comprising deactivated acidic catalyst containing conjunct polymer;
recovering the reaction products;
contacting the deactivated acidic catalyst containing the conjunct polymer with at least one silane or borane compound in a regeneration zone under regeneration conditions, the conjunct polymer reacting with the at least one silane or borane compound resulting in a catalyst phase and an organic phase containing the conjunct polymer and at least one silyl or boryl compound;
separating the catalyst phase from the organic phase;
chemically reducing the at least one silyl or boryl compound to regenerate the at least one silane or borane compound; and
separating the at least one regenerated silane or borane compound from the conjunct polymer.

19. The process of claim 18 wherein contacting the deactivated acidic catalyst containing the conjunct polymer with the at least one silane or borane compound comprises contacting the deactivated acidic catalyst containing the conjunct polymer with the at least one silane or borane compound and a solvent; wherein the solvent is capable of forming a separate phase from the acidic catalyst.

* * * * *